(12) United States Patent
Tseng et al.

(10) Patent No.: US 7,442,328 B2
(45) Date of Patent: Oct. 28, 2008

(54) RETARDANTS ON POLYMERIZATION OF ANILINE

(75) Inventors: Wen-Nan Tseng, Nan Tou Hsien (TW); Li-Duan Tsai, Hsinchu City (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days.

(21) Appl. No.: 11/368,637

(22) Filed: Mar. 7, 2006

(65) Prior Publication Data

US 2006/0202169 A1    Sep. 14, 2006

(30) Foreign Application Priority Data

Mar. 8, 2005 (TW) .............. 94106973 A

(51) Int. Cl.
*H01B 1/00* (2006.01)
*C08G 73/00* (2006.01)

(52) U.S. Cl. .............. 252/500; 528/422

(58) Field of Classification Search .......... 528/422; 252/500

See application file for complete search history.

(56) References Cited

U.S. PATENT DOCUMENTS 5,958,301 A * 9/1999 Angelopoulos et al. ..... 252/500
7,208,104 B2 * 4/2007 Tsai et al. ................... 252/500

FOREIGN PATENT DOCUMENTS

JP   2001-064386   * 3/2001

OTHER PUBLICATIONS

Zhang et al., "Electrochemical copolymerization of aniline with m-aminophenol and novel electrical properties of the copolymer in the wide pH range," Electrochimica Acta, 51, pp. 4262-4270 (2006).*
STN Chemical Registry Abstract No. 22948-02-3.*
STN Chemical Registry Abstract No. 591-27-5.*
STN Chemical registry Abstract No. 108-45-2.*

* cited by examiner

*Primary Examiner*—Jaison P Thomas
(74) *Attorney, Agent, or Firm*—Birch, Stewart, Kolasch & Birch, LLP

(57) ABSTRACT

A series of retardants on polymerization of aniline. The molecular structure of the retardant are aromatic compounds with meta-disubstitution. The two substituents of the retardant could be respectively selected from the group of amino group, hydroxyl group, thiol group, and mixtures thereof. A chemical composition for polyaniline preparation comprising: aniline monomer, oxidant, protic acid, retardant and solvent.

6 Claims, 3 Drawing Sheets

|  | Retardant | Retardant /aniline (%) | Polymerization time (min) | Conductivity (S/cm) |
|---|---|---|---|---|
| First control | No added | 0 | 5.20 | 0.54 |
| Second control | nitrobenzene | 2.0 | 5.50 | 0.48 |
| Embodiment 1 | 3-aminophenol | 0.5 | 11.50 | 0.58 |
| Embodiment 2 | 3-aminophenol | 1.0 | 36.25 | 0.55 |
| Embodiment 3 | 3-aminophenol | 2.0 | 130.75 | 0.66 |

|  | Retardant | Retardant /aniline (%) | Polymerization time (min) | Conductivity (S/cm) |
|---|---|---|---|---|
| First control | No added | 0 | 5.20 | 0.54 |
| Second control | nitrobenzene | 2.0 | 5.50 | 0.48 |
| Embodiment 1 | 3-aminophenol | 0.5 | 11.50 | 0.58 |
| Embodiment 2 | 3-aminophenol | 1.0 | 36.25 | 0.55 |
| Embodiment 3 | 3-aminophenol | 2.0 | 130.75 | 0.66 |

|  | Retardant | Retardant /aniline (%) | Polymerization time (min) | Conductivity (S/cm) |
|---|---|---|---|---|
| First control | No added | 0 | 5.20 | 0.54 |
| Second control | nitrobenzene | 2.0 | 5.50 | 0.48 |
| Embodiment 3 | 3-aminophenol | 2.0 | 130.75 | 0.66 |
| Embodiment 4 | 1,3-diaminobenzene | 2.0 | 75.00 | 0.94 |
| Embodiment 5 | 1,3-dihydroxybenzene | 2.0 | 12.50 | 0.54 |
| Embodiment 6 | 1,3-benzenedithiol | 2.0 | 10.75 | 0.52 |
| Embodiment 7 | 3-aminothiophenol | 2.0 | 85.50 | 0.75 |
| Embodiment 8 | 1,3,5-Trihydroxybenzene | 2.0 | 15.25 | 0.64 |

FIG. 4

RETARDANTS ON POLYMERIZATION OF ANILINE

BACKGROUND OF THE INVENTION (1) Field of the Invention

The invention relates to a series of retardants, and more particularly to a polymerization retardant of aniline and a chemical composition for polyaniline preparation.

(2) Description of the Prior Art

The first conducting polymer was synthesized in 1862, Letherbyl observed the green-blue deposition grown on the platinum electrode by electrolysis of aniline solution. It was named "Aniline black" because it was uncharacterized at that time. In 1986, the conductivity of polyaniline had been increased from $10^{-11}$ S/cm to 10 S/cm by chemical oxidation of aniline in the presence of protic acid. In 1994, MacDiarmid addressed that the conductivity of polyaniline can be brought up to 200 S/cm by using camphorsulfonic acid (CSA) as dopant. The remarkable conductivity of polyaniline makes it more applicable.

Aniline is colorless liquid with boiling point of 184° C. and density of 1.022 $g/cm^3$. It can be polymerized by either electrochemical method or chemical oxidation to produce polyaniline. Polyaniline possesses several nice properties, such as high conductivity, high stability, low cost, simple synthesis process, and structure variety. Those characteristics make polyaniline widely applicable and also the very first commercialized conducting polymer.

Although polyaniline carries such advantages, however, low solubility in solvents make it difficult to do further processing, for example, coating. To avoid that, polyaniline was usually polymerized in situ by applying the solution of aniline monomer and oxidant on the substrate and process polymerization on it directly. In general, aniline monomer would be polymerized rapidly (in few minutes) once mixed with oxidant. While polymerization occurred, polyaniline precipitated from solvent and dramatically increase the viscosity of solution. That means the operating time was limited, solution of aniline monomer and oxidant should be used on substrate in few minutes or it will spoiled. The rapid polymerization rate of aniline is a major problem in many fields, such as in electrolytic capacitor, the most successful application of conducting polymer. The electrode of electrolytic capacitors is a highly porous substrate. The pore size is about 50 nm~2 μm. Conducting polymer was coated on the porous substrate to form a electrolytic capacitor. FIG. 1A~FIG. 1B is showing micro structure of the cross section of capacitor electrode 1. Conducting polymer 2 was coated into the micro pore 11. In the case of too fast polymerization, the viscosity of monomer solution increased rapidly that cause the incomplete coating of conducting polymer 2 and leave vacancy 111. These vacancy 111 would damage the capacitor by lower capacity, lower reliability, and increase the equivalent series resistance (ESR).

Therefore, controlling the aniline polymerization rate is one of the most important points for bringing polyaniline to extensive application.

SUMMARY OF THE INVENTION

The object of the present invention is to provide a series of retardants on polymerization of aniline.

Another object of the present invention is to provide a chemical composition to prepare polyaniline under controlled polymerization rate.

The molecular structure of the retardants in present invention are aromatic compounds with meta-disubstitution in which the two substituents are respectively selected from the group of amino group, hydroxyl group, thiol group, and mixtures thereof.

The chemical composition for polyaniline preparation comprising: aniline monomer, oxidant, protic acid, retardant and solvent.

To sum up, the invention disclosed herein are the retardants on aniline polymerization and a chemical composition for polyaniline preparation. The retardant disclosed are meta-disubstituted benzene and its derivatives, in which the two substituents are respectively selected from the group of amino group, hydroxyl group, thiol group, and mixtures thereof. By using the retardants in the composition, polyaniline can be prepared under controlled polymerization rate. Thus the operating convenience and also the conductivity of polyaniline are greatly improved.

BRIEF DESCRIPTION OF THE DRAWINGS

The present invention will now be specified with reference to its preferred embodiment illustrated in the drawings, in which:

FIG. 4 showed results response of variety embodiments in aniline polymerization.

DESCRIPTION OF THE PREFERRED EMBODIMENT

The invention disclosed herein is directed to a series of polymerization retardants for aniline. And also, a chemical composition for aniline preparation in which containing the retardant. Applying the present invention, aniline polymerization rate is controllable and the conductivity of polyaniline thus prepared is enhanced. In the following description and illustration, numerous details are set forth in order to provide a thorough understanding of the present invention.

Figure 1A:
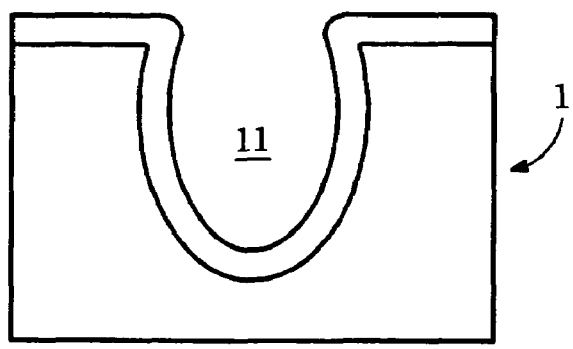
FIG. 1A~B are showing the occurrence of vacancy while coating polyaniline on a porous substrate due to the rapid aniline polymerization rate.
Figure 1B:
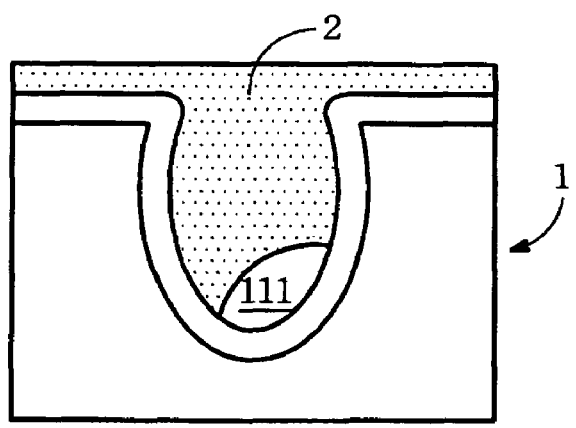
Figure 2:
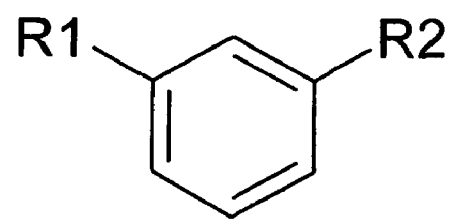
FIG. 2 illustrated the chemical structure for the aniline polymerization retardant which is disclosed by the invention.

The aniline polymerization retardant disclosed by the present invention is meta-disubstituted benzene and derivatives thereof. Please refer to FIG. 2, which demonstrates the basic molecular structure of aniline polymerization retardant disclosed by the present invention. In FIG. 2, R1 and R2 indicate the substituents in aniline polymerization retardant. R1 and R2 can be respectively selected from the group of amino group ($NH_2$), hydroxyl group (OH), thiol group (SH) and the mixture thereof.

Applying the aniline polymerization retardant disclosed by the present invention in aniline polymerization by chemical method doesn't draw the line on the varieties of retardant. It can be the retardant with meta-disubstitution mentioned above or the mixture of varieties of retardants.

The invention disclosed herein is directed to a chemical composition for aniline polymerization and the composition contains: aniline monomer, oxidant, protic acid, retardant and solvent, wherein the molecular structure of the retardant is meta-disubstituted benzene, and the two substituents can be respectively selected from the group of amino group, hydroxyl group, thiol group and mixtures thereof.

The aniline monomer mentioned above includes aniline and its derivatives. The oxidant is selected from the group of persulfate (such as ammonium persulfate, sodium persulfate, potassium persulfate and etc), ferric ion ($Fe^{3+}$), hydrogen peroxide or mixtures thereof. The protic acid is selected from the group of inorganic acid (such as hydrogen chloride, sulfuric acid and perchloric acid and etc), organic acid (such as benzoic acid, toluenesulfonic acid, camphorsulfonic acid and alkyl benzenesulfonic acid and etc) and mixtures thereof. The solvent is chosen according to different polyaniline applying occasions, wherein the solvent is selected from the group of water, alcohols, ketones and mixtures thereof.

The composition of aniline polymerization mentioned above in which the retardant can be composed of meta-disubstituted benzene or its derivatives, wherein there's no limitation for retardant in varieties for polymerization. There are many options for retardants all depend on the desired polymerization rate and conductivity of polyaniline.

In general, the experiment conditions for all the embodiments are as follows: to a 9.0 ml aqueous solution containing 0.5 M aniline, 0.5 M p-toluenesulfonic acid, and various amount of retardant (please refer to FIG. 3A and FIG. 4) was added 6.0 ml aqueous solution containing 0.5 M ammonium persulfate. Aniline polymerization is a exothermal reaction. So, the temperature of the mixture was recorded along with reaction time to monitor the reaction (please refer to FIG. 3B). The point when the highest temperature was reached is defined as polymerization time which means the polymerization was finished. After the polymerization was finished, the mixture was cooled down to 25° C. and the green-black precipitate was filtered and dried to provide polyaniline. The conductivity was examined by four-point probe conductivity meter on the pressed polyaniline pellet.

Figures 3A, 3B:
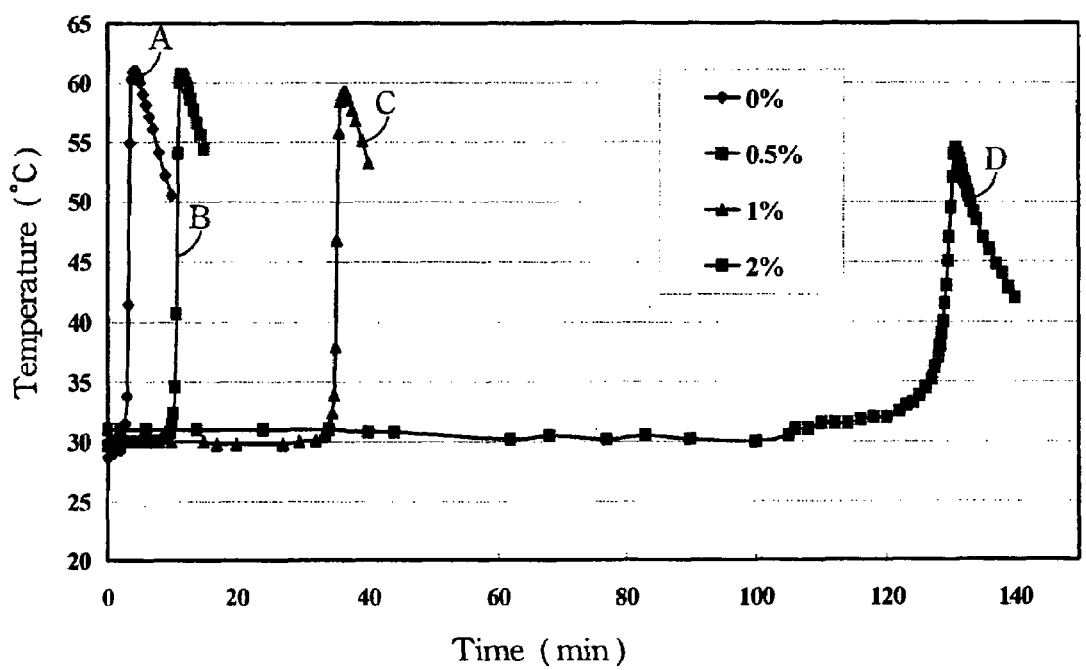
FIG. 3A demonstrated the better results when applying the retardant of the present invention to the polymerization process.
FIG. 3B represented the temperature profile of aniline polymerization with various amount of retardant or without retardant.

Please refer to FIG. 3A~FIG. 3B, which illustrate three better embodiments of the present invention. Herein 3-aminophenol (R1=$NH_2$, R2=OH) is used as the aniline polymerization retardant. There are three embodiments for comparing the polymerization time and conductivity with various proportion of retardant/aniline ranging from 0.5% to 2.0%. Furthermore, there are two control experiments comparing with the three embodiments. The first control is the chemical composition without retardant in the polymerization process and the second control is using the known retardant, nitrobenzene, instead of the present invention in aniline polymerization process.

FIG. 3A showed the polymerization time and conductivities of two control experiments and embodiment 1-3. Indeed, the embodiments of the present invention can retard the polymerization time based on the experiment results but nitrobenzene can only slightly delay the polymerization time and even make it worse in conductivity comparing to the control which is without retardant. The retardant of embodiment 1-3 is very potent that only trace amount of 3-aminophenol (retardant/aniline=0.5%) can double the polymerization time (embodiment 1) without sacrifice the conductivity. Moreover, increasing the ratio of 3-aminophenol/aniline not only controlled the polymerization time effectively but also increase the conductivity comparing to the polyaniline produced without adding any retardant.

FIG. 3B demonstrated the impact of polymerization time with and without retardant. Aniline polymerization is exothermic reaction so that the temperature would increase dramatically in the beginning of polymerization but decrease rapidly in the end of polymerization. The curve A in FIG. 3B represents the first control and curve B~D represent respectively of embodiment 1-3 that have different ratio of retardant/aniline. With the increasing retardant concentration, the aniline polymerization rate had been retarded efficiently. At ratio of 3-aminophenol/aniline=2.0%, the polymerization time had been retarded for 125 minutes. These results demonstrate that user can set the desired polymerization time by changing the concentration of the retardant of the present invention.

Apparently, the results showed in FIG. 3A~FIG. 3B reveal the great difference between the retardant disclosed herein and the conventional retardant in controlling polymerization time and improving conductivity. The potency of the retardant of the present invention on retarding polymerization time and increasing the conductivity is much better than the conventional one. In FIG. 3B, curve B~D showed by controlling the amount of the retardant of the present invention can determine the polymerization time and this improvement helps a lot in practical application. Briefly, results presented herein demonstrate the retardant of the present invention can provide an efficient way to control the polymerization time and make the application of polyaniline more widely.

The retardant disclosed herein is directed to aniline polymerization retardant. The molecular structure of the retardant is meta-disubstituted benzene and derivatives of meta-disubstituted benzene. The two substituents are respectively selected from the functional groups of amino group, hydroxyl group, thiol group and the mixture thereof.

The three functional groups mentioned above were selected through the standard tests. The results of applying the retardant with variety functional groups in polymerization are listed in FIG. 4.

FIG. 4 listed 8 conditions of aniline polymerization. In FIG. 4 there're showing 2 control experiments, the first one is a conventional composition in which is without retardant and the second was adding conventional retardant, nitrobenzene. In FIG. 4, embodiment 3-8 are adding the retardants disclosed by the present invention. In FIG. 4 embodiment 3~8, all the ratios of retardant/aniline are 2.0% but the substituents are different respectively, such as embodiment 3 is 3-aminophenol, embodiment 4 is 1,3-diaminobenzene, embodiment 5 is 1,3-dihydroxybenzene, embodiment 6 is 1,3-benzenedithiol, embodiment 7 is 3-aminothiophenol and embodiment 8 is 1,3,5-trihydroxybenzene.

According to the results, the retardants disclosed by the present invention all can retard the aniline polymerization time. Although different retardants have varied impacts on retarding efficiency, comparing to conventional retardant, nitrobenzene, embodiment 3~8 at least have more than five minutes in retarding time and conductivities are higher than the control one which is without any retardant.

To sum up, the invention disclosed herein is the meta-disubstituted benzene and its derivatives. It can be used as retardant in aniline polymerization and increase the conductivity of polyaniline. Thus the operating convenience and also the properties of polyaniline are greatly improved.

While the present invention has been particularly shown and described with reference to a preferred embodiment, it will be understood by those skilled in the art that various changes in form and detail may be without departing from the spirit and scope of the present invention.

I claim:

1. A chemical composition for polyaniline preparation comprising: aniline monomer, oxidant, protic acid, retardant and solvent, the retardant is 0.5% to 2.0% based on the amount of aniline monomer and used for preparing polyaniline under controlled polymerization rate, wherein the retardant comprising molecular structure of meta-disubstituted benzene, and one of the two substitutients is amino group, and the other one of the two substituents is selected from the group consisting of amino group, hydroxyl group, and thiol group.

2. The chemical composition for polyaniline preparation of claim 1, wherein the aniline monomer including aniline and its derivatives.

3. The chemical composition for polyaniline preparation of claim 1, wherein the oxidant is selected from the group of persulfates, ferric ion, hydrogen peroxide and mixtures thereof.

4. The chemical composition for polyaniline preparation of claim 1, wherein the protic acid is selected from the group of inorganic acid, organic acid and the mixture thereof.

5. The chemical composition for polyaniline preparation of claim 1, wherein the solvent is selected from the group of water, alcohols, ketones and mixture thereof.

6. The chemical composition for polyaniline preparation of claim 1, wherein the retardant is composed of several meta-disubstituted benzene.

\* \* \* \* \*